United States Patent
Chancellor et al.

(10) Patent No.: US 11,291,690 B2
(45) Date of Patent: *Apr. 5, 2022

(54) MUSCLE DERIVED CELLS FOR THE TREATMENT OF GASTRO-ESOPHAGEAL PATHOLOGIES AND METHODS OF MAKING AND USING THE SAME

(71) Applicant: University of Pittsburgh—Of the Commonwealth System of Higher Education, Pittsburgh, PA (US)

(72) Inventors: Michael B. Chancellor, Pittsburgh, PA (US); Jay Pasricha, Ellicott City, MD (US); Ronald Jankowski, Pittsburgh, PA (US); Ryan Pruchnic, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/785,756

(22) Filed: Feb. 10, 2020

(65) Prior Publication Data

US 2021/0000878 A1 Jan. 7, 2021

Related U.S. Application Data

(63) Continuation of application No. 15/801,737, filed on Nov. 2, 2017, now abandoned, which is a continuation of application No. 15/067,351, filed on Mar. 11, 2016, now abandoned, which is a continuation of application No. 13/766,894, filed on Feb. 14, 2013, now abandoned, which is a continuation of application No. 13/550,381, filed on Jul. 16, 2012, now abandoned, which is a continuation of application No. 12/547,149, filed on Aug. 25, 2009, now abandoned, which is a continuation-in-part of application No. 11/959,054, filed on Dec. 18, 2007, now Pat. No. 9,121,009.

(60) Provisional application No. 61/091,569, filed on Aug. 25, 2008, provisional application No. 60/870,516, filed on Dec. 18, 2006.

(51) Int. Cl.
| | | |
|---|---|---|
| *A61K 35/34* | (2015.01) | |
| *C12N 5/077* | (2010.01) | |
| *A61F 2/08* | (2006.01) | |
| *A61F 2/04* | (2013.01) | |
| *A61K 35/12* | (2015.01) | |

(52) U.S. Cl.
CPC ............ *A61K 35/34* (2013.01); *A61F 2/04* (2013.01); *A61F 2/08* (2013.01); *C12N 5/0658* (2013.01); *A61F 2002/044* (2013.01); *A61K 35/12* (2013.01); *A61M 2202/09* (2013.01); *C12N 2500/38* (2013.01); *C12N 2501/105* (2013.01); *C12N 2501/11* (2013.01); *C12N 2501/115* (2013.01); *C12N 2501/165* (2013.01); *C12N 2501/39* (2013.01); *C12N 2501/91* (2013.01); *C12N 2509/00* (2013.01); *C12N 2533/54* (2013.01)

(58) Field of Classification Search
None
See application file for complete search history.

(56) References Cited

U.S. PATENT DOCUMENTS

| | | | |
|---|---|---|---|
| 4,424,208 | A | 1/1984 | Wallace et al. |
| 4,965,353 | A | 10/1990 | della Valle et al. |
| 5,130,141 | A | 7/1992 | Law et al. |
| 5,538,722 | A | 7/1996 | Blau et al. |
| 5,667,778 | A | 9/1997 | Atala |
| 5,858,390 | A | 1/1999 | Boss, Jr. |
| 5,876,447 | A | 3/1999 | Arnett |
| 6,099,832 | A | 8/2000 | Mickle et al. |
| 6,576,264 | B1 | 6/2003 | Henriksen et al. |
| 6,866,842 | B1 | 3/2005 | Chancellor et al. |

(Continued)

FOREIGN PATENT DOCUMENTS

| | | |
|---|---|---|
| WO | WO-1994/025080 A1 | 11/1994 |
| WO | WO-1999/46366 A1 | 9/1999 |

(Continued)

OTHER PUBLICATIONS

[No Authors Listed] Report on autologous fat transplantation. ASPRS Ad-Hoc Committee on New; Procedures, Sep. 30, 1987. Plast Surg Nurs. 1987 Winter;7(4):140-1.

(Continued)

*Primary Examiner* — Allison M Fox
(74) *Attorney, Agent, or Firm* — Goodwin Procter LLP

(57) ABSTRACT

The present invention provides muscle-derived progenitor cells that show long-term survival following transplantation into body tissues and which can augment soft tissue following introduction (e.g. via injection, transplantation, or implantation) into a site of soft tissue. Also provided are methods of isolating muscle-derived progenitor cells, and methods of genetically modifying the cells for gene transfer therapy. The invention further provides methods of using compositions comprising muscle-derived progenitor cells for the augmentation and bulking of mammalian, including human, soft tissues in the treatment of various cosmetic or functional conditions, including malformation, injury, weakness, disease, or dysfunction. In particular, the present invention provides treatments and amelioration of symptoms for gastro-esophageal pathologies like gastro-esophageal reflux.

12 Claims, 6 Drawing Sheets

(56) References Cited

U.S. PATENT DOCUMENTS

| | | | |
|---|---|---|---|
| 6,974,593 | B2 | 12/2005 | Henriksen et al. |
| 7,115,417 | B1* | 10/2006 | Chancellor .......... C12N 5/0658 |
| | | | 435/383 |
| 7,906,110 | B2 | 3/2011 | Chancellor et al. |
| 8,211,423 | B2* | 7/2012 | Chancellor ............ A61K 35/34 |
| | | | 424/93.7 |
| 8,741,277 | B2 | 6/2014 | Chancellor et al. |
| 9,121,009 | B2* | 9/2015 | Chancellor ............. A61P 11/06 |
| 2008/0152627 | A1 | 6/2008 | Chancellor et al. |
| 2009/0010897 | A1 | 1/2009 | Chancellor et al. |
| 2010/0158875 | A1 | 6/2010 | Chancellor et al. |
| 2013/0158662 | A1 | 6/2013 | Chancellor et al. |

FOREIGN PATENT DOCUMENTS

| | | |
|---|---|---|
| WO | WO-1999/056785 A2 | 11/1999 |
| WO | WO-2000/17322 A2 | 3/2000 |
| WO | WO-2000/29552 A1 | 5/2000 |
| WO | WO-2001/78754 A2 | 10/2001 |
| WO | WO-2002/067867 A2 | 9/2002 |
| WO | WO-2004/096245 A2 | 11/2004 |
| WO | WO-2008/066886 A2 | 6/2008 |
| WO | WO-2008/076435 A1 | 6/2008 |

OTHER PUBLICATIONS

Andrews et al. "Monoclonal Antibody 12-8 Recognizes a 115-kd Molecule Present on both Unipotent and Multipotent Hematopoietic Colony-Forming Cells and Their Precursors." Blood. 67.3(1986):842-845.

Anwer et al. "Systemic Effect of Human Growth Hormone After Intramuscular Injection of a Single Dose of a Muscle-Specific Gene Medicine." Hum. Gene Ther. 9(1998):659-670.

Ashman et al. "The Biology of Stem Cell Factor and its Receptor C-kit." Int. J. Biochem. Cell. Biol. 31(1999):1037-1051.

Atkins et al. "Intracardiac Transplantation of Skeletal Myoblasts Yields Two Populations of Striated Cells In Situ." Ann. Thorac. Surg. 67(1999):124-129.

Atkins et al. "Myogenic Cell Transplantation Improves In Vivo Regional Performance in Infarcted Rabbit Myocardium." J. Heart Lung Transplant. 18(1999):1173-1180.

Baroffio et al. "Identification of Self-Renewing Myoblasts in the Progeny of Single Human Muscle Satellite Cells." Differentiation. 60(1996):47-57.

Bartynski et al. "Histopathologic Evaluation of Adipose Autografts in a Rabbit Ear Model." Otolaryngol. Head Neck Surg. 102(1990):314-321.

Beachamp et al. "Dynamics of Myoblast Transplantation Reveal a Discrete Minority of Precursors with Stem Cell-like Properties as the Myogenic Source." J. Cell Biol. 144(1999):1113-1122.

Berjukow et al. "Membrane Properties of Single Muscle Cells of the Rhabdosphincter of ther Male Urethra." Prostate. 58.3(2004):238-247.

Blanton et al. "Isolation of Two Populations of Myoblasts from Porcine Skeletal Muscle." Muscle Nerve. 22(1999):43-50.

Chajchir et al. "Fat Grafting Injection for Soft-Tissue Augmentation." Plast. Reconstr. Surg. 84(1989):921-935.

Chancellor et al. "Preliminary Results of Myoblast Injection Into the Urethra and Bladder Wall: A Possible Method for the Treatment of Stress Urinary Incontinence and Impaired Detrusor Contractility." Neurourol. Urodyn. 19.3(2000):279-287.

Civin et al. "Antigenic Analysis of Hematopiesis: A Hematopoietic Progenitor Cell Surface Antigen Defined by a Monoclonal Antibody Raised against KG-Ia Cells." J. Immunol. 133(1984):157-165.

Crisan et al. "Identification, Purification and Characterization of a Novel Population of cd146+cd133+ Myogenic Cells in Human Skeletal Muscle." Orthopaedic Research Society (ORS) 53rd Annual Meeting. Feb. 12-14, 2007: San Diego, CA (Paper No. 0040).

Dalle et al. "Improvement of Mouse β-thalassemia Upon Erythropoietin Delivery by Encapsulated Myoblasts." Gene Ther. 6(1999):157-161.

Deasy et al. "A Role for Cell Sex in Stem Cell Mediated Skeletal Muscle Regeneration: Female Cells Have Higher Muscle Regeneration Efficiency." J. Cell. Biol. 177.1(2007):73-86.

Dhawan et al. "Systemic Delivery of Human Growth Hormone by Injection of Genetically Engineered Myoblasts." Science. 254(1992):1509-1512.

Ding et al. "Bone Marrow Stromal Cells as a Vehicle for Gone Transfer." Gene Therapy. 6.9(1999):1611-1616.

Dominov et al. "Bcl-2 Expression Identifies an Early Stage of Myogenesis and Promotes Clonal Expansion of Muscle Cells." J. Cell Biol. 142(1998):537-544.

Ersek. "Transplantation of Purified Autologous Fat: A 3-Year Follow-Up is Disappointing." Plast. Reconstr. Surg. 87(1991):219-228.

Fascetti-Leon et al. "Murine Muscle Precursor Cells Survived and Integrated in a Cryoinjured Gastroesophageal Junction." J. Surg. Res. 143.2(2007):253-259.

Faustman et al. "Prevention of Xenograft Rejection by Masking Donor HLA Class I Antigens." Science. 252(1991):1701.

Fina et al. "Expression of the CD34 Gene in Vascular Endothelial Cells." Blood. 75(1990):2417-2426.

Fukuda et al. "Regenerative Medicine and Life Science—Reproductive Engineering, Stem Cell Engineering, and Tissue Engineering." Tanpakushita Kakusan Kouso (Protein, Nucleic Acid and Enzyme). 45.13(2000):2078-2084. (Abstract only in English).

Grinnell. "Trophic Interaction Between Nerve and Muscle." Myology. Engel et al, eds. New York: McGraw-Hill, Inc. 2(1994):303-304.

Gros et al. "Insulin Production by Engineered Muscle Cells." Hum. Gene Ther. 10(1999):1207-1217.

Gussoni et al. "Normal Dystrophin Transcripts Detected in Duchenne Muscular Dystrophy Patients After Myoblast Transplantation." Nature. 356(1992):435-438.

Hortelano et al. "Persistent Delivery of Factor IX in Mice: Gene Therapy for Hemophilia Using Implantable Microcapsules." Hum. Gene Ther. 10(1999):1281-1288.

Huard et al. "Human Myoblast Transplantation: Preliminary Results of 4 Cases." Muscle & Nerve. 15(1992):550-560.

Hörl et al. "Technique for Liposuction Fat Reimplantation and Long-Term Volume Evaluation by Magnetic Resonance Imaging." Ann. Plast. Surg. 26(1991):248-258.

Ikada. "Tissue Engineering—Toward Establishing of Basic Technology and Clinical Applications." Kagaku-Dojin Publishing Co., Inc. (2001)183-191. (English Abstract Only).

International Preliminary Report for Application No. PCT/US2007/025863, dated Jun. 24, 2009.

Irintchev et al. "Expression Patter of M-Cadherin in Normal, Denervated, and Regenerating Mouse Muscles." Dev. Dynam. 199(1994):326-337.

Japanese Office Action for Application No. JP2002-567239, dated Feb. 7, 2007 (with English Translation).

Japanese Pre-Appeal Examination Report for Application No. JP2002-567239, dated Oct. 22, 2007 (with English Translation).

Jiao et al. "Intracerebral Transplants of Primary Muscle Cells: A Potential 'Platform' for Transgene Expression in the Brain." Brain Res. 575(1992):143-147.

Kahrilas. "Thinking Outside the Box: Autotransplantation into GI Sphincters." Gastrointest. Endosc. 70.6(2009):1238-1240.

Karpati et al. "Myoblast Transfer in Duchenne Muscular Dystrophy." Ann. Neurol. 34(1993):8-17.

Katagiri et al. "Bone Morphogenetic Protein-2 Converts the Differentiation Pathway of C2C12 Myoblasts into the Osteoblast Lineage." J. Cell Biol. 127(1994):1755-1766.

Kaufman et al. "Replicating Myoblasts Express a Muscle-Specific Phenotype." PNAS. 85.24(1988):9606-9610.

Koretzky. "Role of the CD45 Tyrosine Phosphatase in Signal Transduction in the Immune System." FASEB J. 7(1993):420-426.

Lipton et al. "Developmental Fate of Skeletal Muscle Satellite Cells." Science. 205(1979): 1292-1294.

(56) References Cited

OTHER PUBLICATIONS

Lynch et al. "Long-Term Expression of Human Adenosine Deaminase in Vascular Smooth Muscle Cells of Rats: A Model for Gene Therapy." PNAS. 89(1992):1138-1142.
Mak et al. "Injectable Filler Materials for Soft-Tissue Augmentation." Otolaryngol. Clin. North. Am. 27(1994):211-222.
Miller et al. "Seeking Muscle Stem Cells." Curr. Top. Dev. Biol. 43(1999):191-219.
Moisset et al. "Expression of Human Dystrophin Following the Transplantation of Genetically Modified mdx Myoblasts." Gene Ther. 5(1998):1340-1346.
Moisset et al. "Successful Transplantation of Genetically Corrected DMD Myoblasts Following ex Vivo Transduction with the Dystrophin Minigene." Biochem. Biophys. Res. Commun. 247(1998):94-99.
Murry et al. "Skeletal Myoblast Transplantation for Repair of Myocardial Necrosis." J. Clin. Invest. 98(1996):2512-2523.
Nguyen et al. "Comparative Study of Survival of Autologous Adipose Tissue Taken and Transplanted by Different Techniques." Plast. Reconstr. Surg. 85(1990):378-389.
Office Action issued for U.S. Appl. No. 111505735, dated Sep. 9, 2009.
Osawa et al. "In Vivo Self-Renewal of c-Kit+ Sca-1+ Linlow/— Hemopoietic Stem Cells." J. Immunol. 156(1996):3207-3214.
Oshima et al. "Differential Myocardial Infarct Repair with Muscle Stem Cells Compared to Myoblasts." Mol. Ther. 12.6(2005):1130-1141.
Oshima et al. "Muscle Stem Cells Provide Superior Infarct Repair When Compared With Myoblasts." Mol. Ther. 11.S1(2005):920.
Oshima et al. "Skeletal Muscle Stem Cells Acquire a Cardiac Phenotype and Display a superior Ability for Cardiac Repair When Compared to Satellite Cells." Jpn. J. Thoracic Cardiovasc. Surg. 52(2004):192.
Partridge et al. "Evidence of Fusion Between Host and Donor Myoblasts in Skeletal Muscle Grafts." Nature. 73(1978):306-308.
Partridge et al. "Myoblast-Based Gene Therapies." Brit. Med. Bullet. 51(1995):123-137.
Pashricha et al. "Endoscopic Injection of Skeletal Muscle-Derived Cells Augments Gut Smooth Muscle Sphincter Function: Implications for a Novel Therapeutic Approach." Gastrointest. Endosc. 70.6(2009):1231-1237.
Payne et al. "A Relationship Between VEGF, Angiogenesis and Cardiac Repair After Muscle Stem Cell Transplantation into Ischemic Hearts." J. Am. College Cardio. 50.17(2007):1677-84.
Payne et al. "Muscle Stem Cells Deliver Dystrophin and Adopt a Cardiac Phenotype Through Both Differentiation and Fusion in the Dystrophic (mdx) Heart." Mol. Ther. 9.SI 1(2004):930.
Payne et al. "Muscle Stem Cells Genetically Modified to Express a VEGF Antagonist Display an Impaired Ability for Cardiac Repair." Mol. Ther. 11.S1(2005):923.
Payne et al. "Muscle-Derived Stem Cells Express a Cardiac Phenotype Upon Transplantation into the Dystrophic Murine Heart." American Heart Association Conference on Molecular Mechanisms of Growth, Death and Regeneration in the Myocardium. 9(2003):p. 42.
Payne et al. "Regeneration of Dystrophin-Expressing Myocytes in the mdx Heart by Skeletal Muscle Stem Cells." Gene Ther. 12.16(2005):1264-1274.
Payne et al. "VEGF Secretion by Skeletal Muscle-Derived Stem Cells Induces Neovascularization, Prevents Remodeling, and Improves Function in Ischemic Heart." Circ. Res. 99.5(2006):p. 17.
Rando et al. "Methods for Myoblast Transplantation." Meth. Cell Biol. 52(1998):261-272.
Regulier et al. "Continuous Delivery of Human and Mouse Erythropoietin in Mice by Genetically Engineered Polymer Encapsulated Myoblasts." Gene Ther. 5(1998):1014-1022.
Roman et al. "Circulating Human or Canine Factor IX From Retrovirally Transduced Primary Myoblasts and Established Myoblast Cell Lines Grafted into Murine Skeletal Muscle." Somat. Cell. Mol. Genet. 18(1992):247-258.
Seale et al. "A New Look at the Origin, Function, and "Stem-Cell" Status of Muscle Satellite Cells." Dev. Biol.218(2000):115-124.
Simmons et al. "CD34 Expression by Stromal Precursors in Normal Human Adult Bone Marrow." Blood. 78(1991):2848-2853.
Supplementary European Search Report for Application No. EP 02706457, dated May 27, 2009.
Torrente et al. "Intraarterial Injection of Muscle-Derived CD34+ Sca-1+ Stem Cells Restores Dystrophin in mdx Mice." J. Cell. Biol. 152.2(2001):335-348.
Tremblay et al. "Results of Triple Blind Clinical Study of Myoblast Transplantations Without Immunosuppressive Treatment in Young Boys with Duchenne Muscular Dystrophy." Cell Transplant. 2(1993):99-112.
Urish et al. "Muscle Stem Cells' High Regenerative Capacity Correlates With a High Resistance to Stress." The Orthopaedic Research Society 52nd Annual Meeting. (Mar. 19-22, 2006), Chicago, IL (Paper No. 0337).
Urish et al. "Oxidative Stress Plays a Major Role in the Differential Repair of Skeletal and Cardiac Muscle Between Muscle Stem Cells and Myoblasts." The Orthopaedic Research Society (ORS) 53rd Annual Meeting (Feb. 12-14, 2007), San Diego, CA (Paper No. 1225).
Urish et al. "The Role of Resistance to Inflammation and Oxidative Stress in Muscle Dtem Cells' Increased Regenerative Capacity." Int. Soc. Stem Cell Res. (Jun. 29-Jul. 1, 2006).
Van de Rijn et al. Mouse Hematopoietic Stem-Cell Antigen Sca-1 is a Member of the Ly-6 Antigen Family. PNAS. 86(1989):4634-4638.
Vandenburgh. "Tissue-Engineered Skeletal Muscle Organoids for Reversible Gene Therapy." Hum. Gene Ther. 7(1996):2195-2200.
Wang et al. "Persistent Systemic Production of Human Factor IX in Mice by Skeletal Myoblast-Mediated Gene Transfer: Feasibility of Repeat Application to Obtain Therapeutic Levels." Blood. 90(1997):1075-1082.
Watt et al. "Long Term Survival of Allografted Muscle Precursor Cells Following a Limited Period of Treatment with Cyclosporin A." Clin. Exp. Immunol. 55(1984):419-426.
Webster et al. "Isolation of Human Myoblasts with the Fluorescence-Activated Cell Sorter." Exp. Cell. Res. 174(1988):252-265.
Yao et al. Primary Myoblast-Mediated Gene Transfer: Persistent Expression of Human Factor IX in Mice. Gene Ther. 1(1994):99-107.
Yokoyama et al. "Myoblast Therapy for Stress Urinary Incontinence and Bladder Dysfunction." World J. Urol. 18(2000):56.61.
Yokoyama et al. "Persistence and Survival of Autologous Muscle Derived Cells Versus Bovine Collagen as Potential Treatment of Stress Urinary Incontinence." J. Urol. 165(2001):76.
Zheng et al. "Multi-Potency of Myo-Endothelial Clones Isolated From Adult Human Skeletal Muscle. NIRA Nominee." The Orthopaedic Research Society (ORS)53rd Annual Meeting. (Feb. 12-14, 2007), San Diego, CA (Paper No. 0421).
Ziegler et al. "KDR Receptor: A Key Marker Defining Hematopoietic Stem Cells." Science. 285(1999):1533-1558.

\* cited by examiner

MUSCLE DERIVED CELLS FOR THE TREATMENT OF GASTRO-ESOPHAGEAL PATHOLOGIES AND METHODS OF MAKING AND USING THE SAME

RELATED APPLICATIONS

This application is a continuation application of U.S. patent application Ser. No. 15/801,737, filed Nov. 2, 2017, which application is a continuation application of U.S. patent application Ser. No. 15/067,351, filed Mar. 11, 2016, which is a continuation application of U.S. patent application Ser. No. 13/766,894, filed Feb. 14, 2013, which is a continuation application of U.S. patent application Ser. No. 13/550,381, filed Jul. 16, 2012, which is a continuation application of U.S. patent application Ser. No. 12/547,149, filed on Aug. 25, 2009, which claims benefit of priority from U.S. Provisional Patent Application No. 61/091,569, filed on Aug. 25, 2008, and which is a continuation-in-part of U.S. patent application Ser. No. 11/959,054 (now U.S. Pat. No. 9,121,009) filed on Dec. 18, 2007, which claims the benefit of priority from U.S. Provisional Application No. 60/870,516, filed on Dec. 18, 2006, contents of each of which are incorporated herein by reference in their entireties.

GOVERNMENT INTERESTS

This invention was made with Government support under Grant No. DK0055387 awarded by the National Institutes of Health. The Government has certain rights to this invention.

FIELD OF THE INVENTION

The present invention relates to muscle-derived progenitor cells (MDC) and compositions of MDCs and their use in the augmentation of body tissues, particularly soft tissue like gastric and esophageal tissue. In particular, the present invention relates to muscle-derived progenitor cells that show long-term survival following introduction into soft tissues, methods of isolating MDCs, and methods of using MDC-containing compositions for the augmentation of human or animal soft tissues, including gastric and esophageal tissue. The invention also relates to novel uses of muscle-derived progenitor cells for the treatment of functional conditions, such as gastro-esophageal reflux disease.

BACKGROUND OF THE INVENTION

Augmentation of soft tissue using synthetic materials such as silicone or polytetrafluoroethylene (PTFE) is well known in the art. U.S. Pat. No. 5,876,447 to Arnett discloses the use of silicone implants for facial plastic surgery. However, such synthetic materials are foreign to the host tissue, and cause an immunological response resulting in the encapsulation of the implant and scarring of the surrounding tissues. Thus, the implant may produce additional functional or aesthetic problems.

Soft tissue augmentation using biopolymers such as collagen or hyaluronic acid has also been described. For example, U.S. Pat. No. 4,424,208 to Wallace et al. discloses methods of augmenting soft tissue utilizing collagen implant material. In addition, U.S. Pat. No. 4,965,353 to della Valle et al. discloses esters of hyaluronic acid that can be used in cosmetic surgery. However, these biopolymers are also foreign to the host tissue, and cause an immunological response resulting in the reabsorption of the injected material. Biopolymers are therefore unable to provide long-term tissue augmentation. Overall, the use of biopolymers or synthetic materials has been wholly unsatisfactory for the purpose of augmenting soft tissue.

Soft tissue augmentation using cell-based compositions has also been developed. U.S. Pat. No. 5,858,390 to Boss, Jr. discloses the use of autologous dermal fibroblasts for the treatment of cosmetic and aesthetic skin defects. Although this treatment avoids the problems inherent in the implantation or injection of synthetic materials or biopolymers, it results in other complications. Because fibroblasts produce collagen, the cells can cause the stiffening and distortion of the tissues surrounding the implant site.

The use of autologous fat cells as an injectable bulking agent has also been described (For review, see K. Mak et al., 1994, Otolaryngol. Clin. North. Am. 27:211 22; American Society of Plastic and Reconstructive Surgery: Report on autologous fat transplantation by the ad hoc committee on new procedures, 1987, Chicago: American Society of Plastic and Reconstructive Surgery; A. Chaichir et al., 1989, Plast. Reconstr. Surg. 84: 921 935; R. A. Ersek, 1991, Plast. Reconstr. Surg. 87:219 228; H. W. Horl et al., 1991, Ann. Plast. Surg. 26:248 258; A. Nguyen et al., 1990, Plast. Reconstr. Surg. 85:378 389; J. Sartynski et al., 1990, Otolaryngol. Head Neck Surg. 102:314 321. However, the fat grafting procedure provides only temporary augmentation, as injected fat is reabsorbed into the host. In addition, fat grafting can result in nodule formation and tissue asymmetry.

Endoscopic delivery of bulking material has been tried for patient suffering from gastro-esophageal reflux disease. However, as the recent recall of ENTERYX® by the FDA suggests, there is a need for a safer treatment of this disease.

Myoblasts, the precursors of muscle fibers, are mononucleated muscle cells that fuse to form post-mitotic multi-nucleated myotubes, which can provide long-term expression and delivery of bioactive proteins (T. A. Partridge and K. E. Davies, 1995, Brit. Med. Bulletin 51:123 137; J. Dhawan et al., 1992, Science 254: 1509 12; A. D. Grinnell, 1994, Myology Ed 2, A. G. Engel and C. F. Armstrong, McGraw-Hill, Inc., 303 304; S. Jiao and J. A. Wolff, 1992, Brain Research 575:143 7; H. Vandenburgh, 1996, Human Gene Therapy 7:2195 2200).

Cultured myoblasts contain a subpopulation of cells that show some of the self-renewal properties of stem cells (A. Baroffio et al., 1996, Differentiation 60:47 57). Such cells fail to fuse to form myotubes, and do not divide unless cultured separately (A. Baroffio et al., supra). Studies of myoblast transplantation (see below) have shown that the majority of transplanted cells quickly die, while a minority survive and mediate new muscle formation (J. R. Beuchamp et al., 1999, J. Cell Biol. 144:1113 1122). This minority of cells shows distinctive behavior, including slow growth in tissue culture and rapid growth following transplantation, suggesting that these cells may represent myoblast stem cells (J. R. Beuchamp et al., supra).

Myoblasts have been used as vehicles for gene therapy in the treatment of various muscle- and non-muscle-related disorders. For example, transplantation of genetically modified or unmodified myoblasts has been used for the treatment of Duchenne muscular dystrophy (E. Gussoni et al., 1992, Nature, 356:435 8; J. Huard et al., 1992, Muscle & Nerve, 15:550 60; G. Karpati et al., 1993, Ann. Neurol., 34:8 17; J. P. Tremblay et al., 1993, Cell Transplantation, 2:99 112; P. A. Moisset et al., 1998, Biochem. Biophys. Res. Commun. 247:94 9; P. A. Moisset et al., 1998, Gene Ther. 5:1340 46). In addition, myoblasts have been genetically engineered- to produce proinsulin for the treatment of Type 1 diabetes (L.

Gros et al., 1999, Hum. Gen. Ther. 10:1207 17); Factor IX for the treatment of hemophilia B (M. Roman et al., 1992, Somat. Cell. Mol. Genet. 18:247 58; S. N. Yao et al., 1994, Gen. Ther. 1:99 107; J. M. Wang et al., 1997, Blood 90:1075 82; G. Hortelano et al., 1999, Hum. Gene Ther. 10:1281 8); adenosine deaminase for the treatment of adenosine deaminase deficiency syndrome (C. M. Lynch et al., 1992, Proc. Natl. Acad. Sci. USA, 89:1138 42); erythropoietin for the treatment of chronic anemia (E. Regulier et al., 1998, Gene Ther. 5:1014 22; B. Dalle et al., 1999, Gene Ther. 6:157 61), and human growth hormone for the treatment of growth retardation (K. Anwer et al., 1998, Hum. Gen. Ther. 9:659 70).

Myoblasts have also been used to treat muscle tissue damage or disease, as disclosed in U.S. Pat. No. 5,130,141 to Law et al., U.S. Pat. No. 5,538,722 to Blau et al., and application U.S. Ser. No. 09/302,896 filed Apr. 30, 1999 by Chancellor et al. In addition, myoblast transplantation has been employed for the repair of myocardial dysfunction (C. E. Murry et al., 1996, J. Clin. Invest. 98:2512 23; B. Z. Atkins et al., 1999, Ann. Thorac. Surg. 67:124 129; B. Z. Atkins et al., 1999, J. Heart Lung Transplant. 18:1173 80).

In spite of the above, in most cases, primary myoblast-derived treatments have been associated with low survival rates of the cells following transplantation due to migration and/or phagocytosis. To circumvent this problem, U.S. Pat. No. 5,667,778 to Atala discloses the use of myoblasts suspended in a liquid polymer, such as alginate. The polymer solution acts as a matrix to prevent the myoblasts from migrating and/or undergoing phagocytosis after injection. However, the polymer solution presents the same problems as the biopolymers discussed above. Furthermore, the Atala patent is limited to uses of myoblasts in only muscle tissue, but no other tissue.

Thus, there is a need for other, different soft tissue augmentation materials that are long-lasting, compatible with a wide range of host tissues, and which cause minimal inflammation, scarring, and/or stiffening of the tissues surrounding the implant site. Accordingly, the muscle-derived progenitor cell-containing compositions of the present invention are provided as improved and novel materials for augmenting soft tissues. Further provided are methods of producing muscle-derived progenitor cell compositions that show long-term survival following transplantation, and methods of utilizing MDCs and compositions containing MDCs to treat various aesthetic and/or functional defects, including, for example, dermatological conditions or injury, and muscle weakness, injury, disease, or dysfunction.

It is notable that prior attempts to use myoblasts for non-muscle soft tissue augmentation were unsuccessful (U.S. Pat. No. 5,667,778 to Atala). Therefore, the findings disclosed herein are unexpected, as they show that the muscle-derived progenitor cells according to the present invention can be successfully transplanted into non-muscle and muscle soft tissue, including epithelial tissue, and exhibit long-term survival. As a result, MDCs and compositions comprising MDCs can be used as a general augmentation material for muscle or non-muscle soft tissue augmentation, as well as for bone production. Moreover, since the muscle-derived progenitor cells and compositions of the present invention can be derived from autologous sources, they carry a reduced risk of immunological complications in the host, including the reabsorption of augmentation materials, and the inflammation and/or scarring of the tissues surrounding the implant site.

SUMMARY OF THE INVENTION

It is an object of the present invention to provide novel muscle-derived progenitor cells (MDCs) and MDC compositions exhibiting long-term survival following transplantation. The MDCs of this invention and compositions containing the MDCs comprise early progenitor muscle cells, i.e., muscle-derived stem cells, that express progenitor cell markers, such as desmin, M-cadherin, MyoD, myogenin, CD34, and Bcl-2. In addition, these early progenitor muscle cells express the Flk-1, Sca-1, MNF, and c-met cell markers, but do not express the CD45 or c-Kit cell markers.

It is another object of the present invention to provide methods for isolating and enriching muscle-derived progenitor cells from a starting muscle cell population. These methods result in the enrichment of MDCs that have long-term survivability after transplantation or introduction into a site of soft tissue. The MDC population according to the present invention is particularly enriched with cells that express progenitor cell markers, such as desmin, M-cadherin, MyoD, myogenin, CD34, and Bcl-2. This MDC population also expresses the Flk-1, Sca-1, MNF, and c-met cell markers, but does not express the CD45 or c-Kit cell markers.

It is yet another object of the present invention to provide methods of using MDCs and compositions comprising MDCs for the augmentation of muscle soft tissue, or non-muscle soft tissue, including smooth muscle, and various organ tissues, without the need for polymer carriers or special culture media for transplantation. Such methods include the administration of MDC compositions by introduction into soft tissue, for example by direct injection into tissue, or by systemic distribution of the compositions. Preferably, soft tissue includes non-bone body tissues. More preferably, soft tissue includes non-striated muscle and non-bone body tissues. Most preferably, soft tissue includes non-muscle, non-bone body tissues. As used herein, augmentation refers to filling, bulking, supporting, enlarging, extending, or increasing the size or mass of body tissue.

It is another object of the present invention to provide methods of augmenting soft tissue, either muscle-derived soft tissue, or non-muscle-derived soft tissue, following injury, wounding, surgeries, traumas, non-traumas, or other procedures that result in fissures, openings, depressions, wounds, and the like, in the skin or in internal soft tissues or organs.

It is yet another object of the present invention to provide MDC-based treatments for gastroesophageal reflux symptoms and conditions. Pharmaceutical compositions comprising MDCs and compositions comprising MDCs may be used for the treatment of gastro-esophageal pathologies. These pharmaceutical compositions comprise isolated MDCs. These MDCs may be subsequently expanded by cell culture after isolation. In one embodiment of the invention, these MDCs are frozen prior to delivery to a subject in need of the pharmaceutical composition.

In one embodiment, when the MDCs and compositions thereof are used to treat gastroesophageal reflux they are injected directly into the esophagus. Preferably, they may be injected into the lower esophageal sphincter. In another embodiment, MDCs and compositions thereof are used to improve at least one symptom of gastro-esophageal reflux disease. These symptoms include heart burn, asthma, acid reflux, persistent sore throat, hoarseness, chronic cough, chest pain, and feeling like there is a lump in the throat.

MDCs are isolated from a biopsy of skeletal muscle. In one embodiment, the skeletal muscle from the biopsy may be stored for 1-6 days. In one aspect of this embodiment, the skeletal muscle from the biopsy is stored at 4° C. The MDCs are then isolated using the pre-plate or the single plate technique.

Using the pre-plate technique, a suspension of skeletal muscle cells from skeletal muscle tissue is plated in a first container to which fibroblast cells of the skeletal muscle cell suspension adhere. Non-adherent cells are then re-plated in a second container, wherein the step of re-plating is after about 15 to about 20% of cells have adhered to the first container. This replating step must be repeated at least once. The MDCs are thereby isolated and may be administered to the esophagus of the mammalian subject.

Using the single plate technique, the cells are minced, and digested using a collagenase, dispase, another enzyme or a combination of enzymes. After washing the enzyme from the cells, the cells are cultured in a flask in culture medium for between about 30 and about 120 minutes. During this period of time, the "rapidly adhering cells" stick to the walls of the flask or container, while the "slowly adhering cells" or MDCs remain in suspension. The "slowly adhering cells" are transferred to a second flask or container and cultured therein for a period of 1-3 days. During this second period of time the "slowly adhering cells" or MDCs stick to the walls of the second flask or container.

In another embodiment of the invention, these MDCs are expanded to any number of cells. In a preferred aspect of this embodiment, the cells are expanded in new culture media for between about 10 and 20 days. More preferably, the cells are expanded for 17 days.

The MDCs, whether expanded or not expanded, may be preserved in order to be transported or stored for a period of time before use. In one embodiment, the MDCs are frozen. Preferably, the MDCs are frozen at between about −20 and −90° C. More preferably, the MDCs are frozen at about −80° C. These frozen MDCs are used as a pharmaceutical composition.

It is yet another object of the present invention to provide MDC-based treatments for increase of lower esophageal sphincter pressure that the lower esophageal sphincter can exert. Pharmaceutical compositions comprising MDCs and compositions comprising MDCs may be used for the increase of lower esophageal sphincter pressure. These pharmaceutical compositions comprise isolated MDCs. These MDCs may be subsequently expanded by cell culture after isolation. In one embodiment of the invention, these MDCs are frozen prior to delivery to a subject in need of the pharmaceutical composition.

In one embodiment, when the MDCs and compositions thereof are used to increase the lower esophageal sphincter pressure in a mammalian subject, they are injected directly into the esophagus. Preferably, they may be injected into the lower esophageal sphincter. In another embodiment, MDCs and compositions thereof are used to increase the lower esophageal sphincter pressure in a mammalian subject at least 10%, or more preferably 20%, or more preferably 30% or more preferably 40% or more preferably 50% or more preferably 60%, or more preferably 70%, or more preferably 80% or more preferably 90% or more preferably 100% or more preferably 110%.

MDCs are isolated from a biopsy of skeletal muscle. In one embodiment, the skeletal muscle from the biopsy may be stored for 1-6 days. In one aspect of this embodiment, the skeletal muscle from the biopsy is stored at 4° C. The MDCs are then isolated using the pre-plate or the single plate technique.

Using the pre-plate technique, a suspension of skeletal muscle cells from skeletal muscle tissue is plated in a first container to which fibroblast cells of the skeletal muscle cell suspension adhere. Non-adherent cells are then re-plated in a second container, wherein the step of re-plating is after about 15 to about 20% of cells have adhered to the first container. This replating step must be repeated at least once. The MDCs are thereby isolated and may be administered to the esophagus of the mammalian subject.

Using the single plate technique, the cells are minced, and digested using a collagenase, dispase, another enzyme or a combination of enzymes. After washing the enzyme from the cells, the cells are cultured in a flask in culture medium for between about 30 and about 120 minutes. During this period of time, the "rapidly adhering cells" stick to the walls of the flask or container, while the "slowly adhering cells" or MDCs remain in suspension. The "slowly adhering cells" are transferred to a second flask or container and cultured therein for a period of 1-3 days. During this second period of time the "slowly adhering cells" or MDCs stick to the walls of the second flask or container.

In another embodiment of the invention, these MDCs are expanded to any number of cells. In a preferred aspect of this embodiment, the cells are expanded in new culture media for between about 10 and 20 days. More preferably, the cells are expanded for 17 days.

The MDCs, whether expanded or not expanded, may be preserved in order to be transported or stored for a period of time before use. In one embodiment, the MDCs are frozen. Preferably, the MDCs are frozen at between about −20 and −90° C. More preferably, the MDCs are frozen at about −80° C. These frozen MDCs are used as a pharmaceutical composition.

Additional objects and advantages afforded by the present invention will be apparent from the detailed description and exemplification hereinbelow.

BRIEF DESCRIPTION OF THE DRAWINGS

The appended drawings of the figures are presented to further describe the invention and to assist in its understanding through clarification of its various aspects.

FIG. 1A shows injected tissues at 100× magnification; FIG. 1B shows injected tissues at 40× magnification. FIGS. 1A and 1B demonstrates that MDC injections maintained the lower esophageal sphincter and anal sphincter soft tissue augmentation for up to 3 days following injection.

FIG. 2A shows a DiI labeled micrograph. FIG. 2B shows a DiI labeled, a smooth muscle actin labeled and a merged micrograph from left to right. FIG. 2C shows a DiI labeled, skeletal muscle myosin labeled and a merged micrograph from left to right.

DETAILED DESCRIPTION OF THE INVENTION

Muscle-Derived Cells and Compositions

Figure 1A:
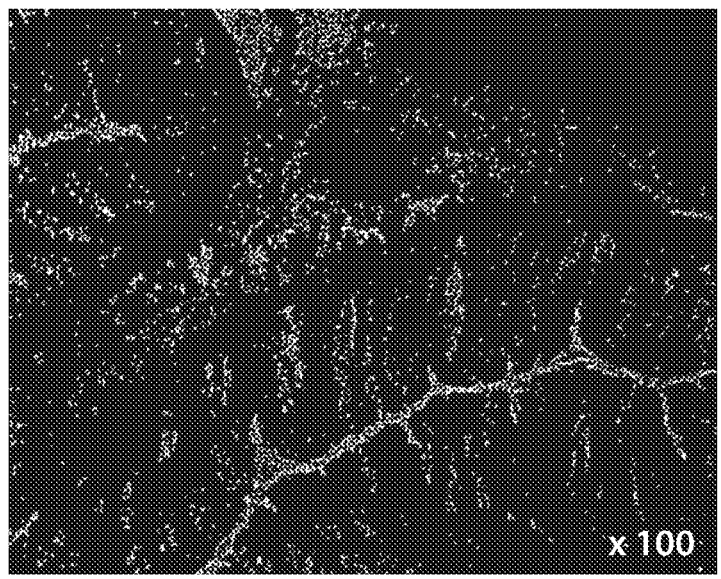
FIGS. 1A and 1B illustrate the results of lower esophageal (FIG. 1A) and anal sphincter (FIG. 1B) soft tissue augmentation utilizing injections of MDCs compositions. Injections were made into the gastroesophageal junction or anal sphincter. At day 3 post-injection, tissue samples were obtained and prepared for analysis. MDCs are indicated by β-galactosidase staining.

The present invention provides MDCs comprised of early progenitor cells (also termed muscle-derived progenitor cells or muscle-derived stem cells herein) that show long-term survival rates following transplantation into body tissues, preferably soft tissues. To obtain the MDCs of this invention, a muscle explant, preferably skeletal muscle, is obtained from an animal donor, preferably from a mammal, including rats, dogs and humans. This explant serves as a structural and functional syncytium including "rests" of muscle precursor cells (T. A. Partridge et al., 1978, Nature 73:306 8; B. H. Lipton et al., 1979, Science 205:12924).

Cells isolated from primary muscle tissue contain mixture of fibroblasts, myoblasts, adipocytes, hematopoietic, and muscle-derived progenitor cells. The progenitor cells of a muscle-derived population can be enriched using differential adherence characteristics of primary muscle cells on collagen coated tissue flasks, such as described in U.S. Pat. No. 6,866,842 of Chancellor et al. Cells that are slow to adhere tend to be morphologically round, express high levels of desmin, and have the ability to fuse and differentiate into multinucleated myotubes U.S. Pat. No. 6,866,842 of Chancellor et al.). A subpopulation of these cells was shown to respond to recombinant human bone morphogenic protein 2 (rhBMP-2) in vitro by expressing increased levels of alkaline phosphatase, parathyroid hormone dependent 3',5'-cAMP, and osteogenic lineage and myogenic lineages (U.S. Pat. No. 6,866,842 of Chancellor et al.; T. Katagiri et al., 1994, J. Cell Biol., 127:1755 1766).

In one embodiment of the invention, a preplating procedure may be used to differentiate rapidly adhering cells from slowly adhering cells (MDCs). In accordance with the present invention, populations of rapidly adhering cells (PP1-4) and slowly adhering, round MDCs (PP6) were isolated and enriched from skeletal muscle explants and tested for the expression of various markers using immunohistochemistry to determine the presence of pluripotent cells among the slowly adhering cells (Example 1; patent application U.S. Ser. No. 09/302,896 of Chancellor et al.). The PP6 cells expressed myogenic markers, including desmin, MyoD, and Myogenin. The PP6 cells also expressed c-met and MNF, two genes which are expressed at an early stage of myogenesis (J. B. Miller et al., 1999, Curr. Top. Dev. Biol. 43:191 219). The PP6 showed a lower percentage of cells expressing M-cadherin, a satellite cell-specific marker (A. Irintchev et al., 1994, Development Dynamics 199:326 337), but a higher percentage of cells expressing Bcl-2, a marker limited to cells in the early stages of myogenesis (J. A. Dominov et al., 1998, J. Cell Biol. 142:537 544). The PP6 cells also expressed CD34, a marker identified with human hematopoietic progenitor cells, as well as stromal cell precursors in bone marrow (R. G. Andrews et al., 1986, Blood 67:842 845; C. I. Civin et al., 1984, J. Immunol. 133:157 165; L. Fina et al, 1990, Blood 75:2417 2426; P. J. Simmons et al., 1991, Blood 78:2848 2853). The PP6 cells also expressed Flk-1, a mouse homologue of human KDR gene which was recently identified as a marker of hematopoietic cells with stem cell-like characteristics (B. L. Ziegler et al., 1999, Science 285:1553 1558). Similarly, the PP6 cells expressed Sca-1, a marker present in hematopoietic cells with stem cell-like characteristics (M. van de Rijn et al., 1989, Proc. Natl. Acad. Sci. USA 86:4634 8; M. Osawa et al., 1996, J. Immunol. 156:3207 14). However, the PP6 cells did not express the CD45 or c-Kit hematopoietic stem cell markers (reviewed in L K. Ashman, 1999, Int. J. Biochem. Cell. Biol. 31:1037 51; G. A. Koretzky, 1993, FASEB J. 7:420 426).

One embodiment of the present invention is the PP6 population of muscle-derived progenitor cells having the characteristics described herein. These muscle-derived progenitor cells express the desmin, CD34, and Bcl-2 cell markers. In accordance with the present invention, the PP6 cells are isolated by the techniques described herein (Example 1) to obtain a population of muscle-derived progenitor cells that have long-term survivability following transplantation. The PP6 muscle-derived progenitor cell population comprises a significant percentage of cells that express progenitor cell markers such as desmin, CD34, and Bcl-2. In addition, PP6 cells express the Flk-1 and Sca-1 cell markers, but do not express the CD45 or c-Kit markers. Preferably, greater than 95% of the PP6 cells express the desmin, Sca-1, and Flk-1 markers, but do not express the CD45 or c-Kit markers. It is preferred that the PP6 cells are utilized within about 1 day or about 24 hours after the last plating.

In a preferred embodiment, the rapidly adhering cells and slowly adhering cells (MDCs) are separated from each other using a single plating technique. One such technique is described in Example 2. First, cells are provided from a skeletal muscle biopsy. The biopsy need only contain about 100 mg of cells. Biopsies ranging in size from about 50 mg to about 500 mg are used in certain embodiments according to both the pre-plating and single plating methods of the invention. Further, biopsies of 50, 100, 110, 120, 130, 140, 150, 200, 250, 300, 400 and 500 mg may be used according to both the pre-plating and single plating methods of the invention.

In a preferred embodiment of the invention, the tissue from the biopsy is then stored for 1 to 7 days. This storage is at a temperature from about room temperature to about 4° C. This waiting period causes the biopsied skeletal muscle tissue to undergo stress. While this stress is not necessary for the isolation of MDCs using this single plate technique, it seems that using the wait period results in a greater yield of MDCs.

Tissue from the biopsies is minced and centrifuged. The pellet is resuspended and digested using a digestion enzyme. Enzymes that may be used include collagenase, dispase or combinations of these enzymes. After digestion, the enzyme is washed off of the cells. The cells are transferred to a flask in culture media for the isolation of the rapidly adhering cells. Many culture media may be used. Particularly preferred culture media include those that are designed for culture of endothelial cells including Cambrex Endothelial Growth Medium. This medium may be supplemented with other components including fetal bovine serum, IGF-1, bFGF, VEGF, EGF, hydrocortisone, heparin, and/or ascorbic acid. Other media that may be used in the single plating technique include InCell M310F medium. This medium may be supplemented as described above, or used unsupplemented.

The step for isolation of the rapidly adhering cells may require culture in flask for a period of time from about 30 to about 120 minutes. The rapidly adhering cells adhere to the flask in 30, 40, 50, 60, 70, 80, 90, 100, 110 or 120 minutes. After they adhere, the slowly adhering cells are separated from the rapidly adhering cells from removing the culture media from the flask to which the rapidly adhering cells are attached to.

The culture medium removed from this flask is then transferred to a second flask. The cells may be centrifuged and resuspended in culture medium before being transferred to the second flask. The cells are cultured in this second flask for between 1 and 3 days. Preferably, the cells are cultured for two days. During this period of time, the slowly adhering cells (MDCs) adhere to the flask. After the MDCs have adhered, the culture media is removed and new culture media is added so that the MDCs can be expanded in number. The MDCs may be expanded in number by culturing them for from about 10 to about 20 days. The MDCs may be expanded in number by culturing them for 10, 11, 12, 13, 14, 15, 16, 17, 18, 19 or 20 days. Preferably, the MDCs are subject to expansion culture for 17 days.

As an alternative to the pre-plating and single plating methods, the MDCs of the present invention can be isolated by fluorescence-activated cell sorting (FACS) analysis using labeled antibodies against one or more of the cell surface markers expressed by the MDCs (C. Webster et al., 1988, Exp. Cell. Res. 174:252 65; J. R. Blanton et al., 1999, Muscle Nerve 22:43 50). For example, FACS separation can be performed using labeled antibodies to directed to CD34, Flk-1, Sca-1, and/or the other cell-surface markers described herein to select a population of PP6-like cells that exhibit long-term survivability when introduced into the host tissue. Also encompassed by the present invention is the use of one or more fluorescence-detection labels, for example, fluorescein or rhodamine, for antibody detection of different cell marker proteins.

Using any of the MDCs isolation methods described above, MDCs that are to be transported, or are not going to be used for a period of time may be preserved using methods known in the art. More specifically, the isolated MDCs may be frozen to a temperature ranging from about −25 to about −90° C. Preferably, the MDCs are frozen at about −80° C., on dry ice for delayed use or transport. The freezing may be done with any cryopreservation medium known in the art.

Muscle-Derived Cell-Based Treatments

In one embodiment of the present invention, the MDCs are isolated from a skeletal muscle source and introduced or transplanted into a muscle or non-muscle soft tissue site of interest. Advantageously, the MDCs of the present invention are isolated and enriched to contain a large number of progenitor cells showing long-term survival following transplantation. In addition, the muscle-derived progenitor cells of this invention express a number of characteristic cell markers, such desmin, CD34, and Bcl-2. Furthermore, the muscle-derived progenitor cells of this invention express the Sca-1, and Flk-1 cell markers, but do not express the CD45 or c-Kit cell markers (see Example 1).

MDCs and compositions comprising MDCs of the present invention can be used to repair, treat, or ameliorate various aesthetic or functional conditions (e.g. defects) through the augmentation of muscle or non-muscle soft tissues. In particular, such compositions can be used as soft-tissue bulking agents for the treatment of gastroesophageal reflux symptoms or conditions.

For MDC-based treatments, a skeletal muscle explant is preferably obtained from an autologous or heterologous human or animal source. An autologous animal or human source is more preferred. MDC compositions are then prepared and isolated as described herein. To introduce or transplant the MDCs and/or compositions comprising the MDCs according to the present invention into a human or animal recipient, a suspension of mononucleated muscle cells is prepared. Such suspensions contain concentrations of the muscle-derived progenitor cells of the invention in a physiologically-acceptable carrier, excipient, or diluent. For example, suspensions of MDCs for administering to a subject can comprise $10^8$ to $10^9$ cells/ml in a sterile solution of complete medium modified to contain the subject's serum, as an alternative to fetal bovine serum. Alternatively, MDC suspensions can be in serum-free, sterile solutions, such as cryopreservation solutions (Celox Laboratories, St. Paul, Minn.) The MDC suspensions can then be introduced e.g., via injection, into one or more sites of the donor tissue.

The described cells can be administered as a pharmaceutically or physiologically acceptable preparation or composition containing a physiologically acceptable carrier, excipient, or diluent, and administered to the tissues of the recipient organism of interest, including humans and non-human animals. The MDC-containing composition can be prepared by resuspending the cells in a suitable liquid or solution such as sterile physiological saline or other physiologically acceptable injectable aqueous liquids. The amounts of the components to be used in such compositions can be routinely determined by those having skill in the art.

The MDCs or compositions thereof can be administered by placement of the MDC suspensions onto absorbent or adherent material, i.e., a collagen sponge matrix, and insertion of the MDC-containing material into or onto the site of interest. Alternatively, the MDCs can be administered by parenteral routes of injection, including subcutaneous, intravenous, intramuscular, and intrasternal. Other modes of administration include, but are not limited to, intranasal, intrathecal, intracutaneous, percutaneous, enteral, and sublingual. In one embodiment of the present invention, administration of the MDCs can be mediated by endoscopic surgery.

For injectable administration, the composition is in sterile solution or suspension or can be resuspended in pharmaceutically- and physiologically-acceptable aqueous or oleaginous vehicles, which may contain preservatives, stabilizers, and material for rendering the solution or suspension isotonic with body fluids (i.e. blood) of the recipient. Non-limiting examples of excipients suitable for use include water, phosphate buffered saline, pH 7.4, 0.15 M aqueous sodium chloride solution, dextrose, glycerol, dilute ethanol, and the like, and mixtures thereof. Illustrative stabilizers are polyethylene glycol, proteins, saccharides, amino acids, inorganic acids, and organic acids, which may be used either on their own or as admixtures. The amounts or quantities, as well as the routes of administration used, are determined on an individual basis, and correspond to the amounts used in similar types of applications or indications known to those of skill in the art.

To optimize transplant success, the closest possible immunological match between donor and recipient is desired. If an autologous source is not available, donor and recipient Class I and Class II histocompatibility antigens can be analyzed to determine the closest match available. This minimizes or eliminates immune rejection and reduces the need for immunosuppressive or immunomodulatory therapy. If required, immunosuppressive or immunomodulatory therapy can be started before, during, and/or after the transplant procedure. For example, cyclosporin A or other immunosuppressive drugs can be administered to the transplant recipient. Immunological tolerance may also be induced prior to transplantation by alternative methods known in the art (D. J. Watt et al., 1984, Clin. Exp. Immunol. 55:419; D. Faustman et al., 1991, Science 252:1701).

Consistent with the present invention, the MDCs are administered to the digestive system (i.e., mouth, tongue, esophagus, stomach, liver, pancreas, gall bladder, intestine, anus, etc.).

Conditions of the lumen: In another embodiment, the MDCs and compositions thereof according to the present invention have further utility as treatments for conditions of the lumen in an animal or mammal subject, including humans. Specifically, the muscle-derived progenitor cells are used for completely or partially blocking, enhancing, enlarging, sealing, repairing, bulking, or filling various biological lumens or voids within the body. Lumens include, without limitation, intestine, stomach and esophagus. Voids may include, without limitation, various tissue wounds (i.e., loss of muscle and soft tissue bulk due to trauma; destruction of soft tissue due to penetrating projectiles such as a stab wound or bullet wound; loss of soft tissue from disease or tissue death due to surgical removal of the tissue), lesions, fissures, diverticulae, cysts, fistulae, and other undesirable or unwanted depressions or openings that may exist within the body of an animal or mammal, including humans. For the treatment of conditions of the lumen, the MDCs are prepared as disclosed herein and then administered, e.g. via injection or intravenous delivery, to the lumenal tissue to fill or repair the void. The number of MDCs introduced is modulated to repair large or small voids in a soft tissue environment, as required.

Conditions of the sphincter: The MDCs and compositions thereof according to the present invention can also be used for the treatment of a sphincter injury, weakness, disease, or dysfunction in an animal or mammal, including humans. In particular, the MDCs are used to augment tissues of the esophageal, anal and pyloric sphincter. Preferably, the sphincter is the lower esophageal sphincter. More specifically, the present invention provides soft tissue augmentation treatments for gastroesophageal reflux symptoms. For the treatment of sphincter defects, the MDCs are prepared as described herein and then administered to the sphincter tissue, e.g. via injection, to provide additional bulk, filler, or support. The number of MDCs introduced is modulated to provide varying amounts of bulking material as required. For example, about 1 to about $5 \times 10^6$ MDCs are used to provide augmentation for an approximately 5 mm region of the gastroesophageal junction or an approximately 5-10 mm region of the anal sphincter (see Example 3). The cells can be engrafted so as to reside within the muscle wall and/or muscularis mucosa of the treated sphincter region. As well, in the treatment of a lower esophageal sphincter, the cellular grafting can be effective to increase the pressure of the sphincter, and/or to reduce acid reflux into the esophagus, e.g. as measured by the fraction of time that the affected lower esophagus exhibits a pH of less than about 4.

Muscle augmentation and contractility: In yet another embodiment of the present invention, the MDCs and compositions thereof are used for the treatment of muscle conditions in a human or animal subject. In particular, the MDCs can be used to augment smooth muscles to treat weakness or dysfunction caused by injury, disease, inactivity, or anoxia- or surgery-induced trauma.

For muscle augmentation or treatment of muscle-related conditions, the MDCs are prepared as described above and are administered, e.g. via injection, into muscle tissue to provide additional bulk, filler, or support. As is appreciated by the skilled practitioner, the number of MDCs introduced is modulated to provide varying amounts of bulking material, as needed or required.

In addition, the MDCs and compositions thereof can be used to affect contractility in smooth muscle tissue, such as gastrointestinal tissue, and esophageal tissue, as example. The present invention also embraces the use of MDCs of the invention in restoring muscle contraction, and/or ameliorating or overcoming smooth muscle contractility problems, such decreased gastrointestinal motility, including the esophagus, stomach and intestine smooth muscle. A specific, yet nonlimiting example of a condition that the MDCs of the invention can improve, reduce, or correct is gastroparesis, i.e., poor motility and emptying of the stomach.

EXAMPLES

Example 1. MDC Enrichment, Isolation and Analysis According to the Pre-Plating Method Enrichment and isolation of MDCs: MDCs were prepared as described (U.S. Pat. No. 6,866,842 of Chancellor et al.). Muscle explants were obtained from the hind limbs of a number of sources, namely from 3-week-old mdx (dystrophic) mice (C57BL/10ScSn mdx/mdx, Jackson Laboratories), 4 6 week-old normal female SD (Sprague Dawley) rats, or SCID (severe combined immunodeficiency) mice. The muscle tissue from each of the animal sources was dissected to remove any bones and minced into a slurry. The slurry was then digested by 1 hour serial incubations with 0.2% type XI collagenase, dispase (grade II, 240 unit), and 0.1% trypsin at 37° C. The resulting cell suspension was passed through 18, 20, and 22 gauge needles and centrifuged at 3000 rpm for 5 minutes. Subsequently, cells were suspended in growth medium (DMEM supplemented with 10% fetal bovine serum, 10% horse serum, 0.5% chick embryo extract, and 2% penicillin/streptomycin). Cells were then preplated in collagen-coated flasks (U.S. Pat. No. 6,866,842 of Chancellor et al.). After approximately 1 hour, the supernatant was removed from the flask and re-plated into a fresh collagen-coated flask. The cells which adhered rapidly within this 1 hour incubation were mostly fibroblasts (Z. Qu et al., supra; U.S. Pat. No. 6,866,842 of Chancellor et al.). The supernatant was removed and re-plated after 30-40% of the cells had adhered to each flask. After approximately 5-6 serial platings, the culture was enriched with small, round cells, designated as PP6 cells, which were isolated from the starting cell population and used in further studies. The adherent cells isolated in the early platings were pooled together and designated as PP1-4 cells.

The mdx PP1-4, mdx PP6, normal PP6, and fibroblast cell populations were examined by immunohistochemical analysis for the expression of cell markers. The results of this analysis are shown in Table 1.

TABLE 1

Cell markers expressed in PP1-4 and PP6 cell populations.

| | mdx PP1-4 cells | mdx PP6 cells | nor PP6 cells | fibroblasts |
|---|---|---|---|---|
| desmin | +/− | + | + | − |
| CD34 | − | + | + | − |
| Bcl-2 | (−) | + | + | − |
| Flk-1 | na | + | + | − |
| Sca-1 | na | + | + | − |
| M-cadherin | −/+ | −/+ | −/+ | − |

TABLE 1-continued

Cell markers expressed in PP1-4 and PP6 cell populations.

| | mdx PP1-4 cells | mdx PP6 cells | nor PP6 cells | fibroblasts |
|---|---|---|---|---|
| MyoD | −/+ | +/− | +/− | − |
| myogenin | −/+ | +/− | +/− | − |

Mdx PP1-4, mdx PP6, normal PP6, and fibroblast cells were derived by preplating technique and examined by immunohistochemical analysis. "−" indicates less than 2% of the cells showed expression; "(−)"; "−/+" indicates 5-50% of the cells showed expression; "+/−" indicates ~40-80% of the cells showed expression; "+" indicates that >95% of the cells showed expression; "nor" indicates normal cells; "na" indicates that the immunohistochemical data is not available.

It is noted that both mdx and normal mice showed identical distribution of all of the cell markers tested in this assay. Thus, the presence of the mdx mutation does not affect the cell marker expression of the isolated PP6 muscle-cell derived population.

MDCs were grown in proliferation medium containing DMEM (Dulbecco's Modified Eagle Medium) with 10% FBS (fetal bovine serum), 10% HS (horse serum), 0.5% chick embryo extract, and 1% penicillin/streptomycin, or fusion medium containing DMEM supplemented with 2% fetal bovine serum and 1% antibiotic solution. All media supplies were purchased through Gibco Laboratories (Grand Island, N.Y.).

Example 2. MDC Enrichment, Isolation and Analysis According to the Single Plate Method Populations of rapidly- and slowly-adhering MDCs were isolated from skeletal muscle of a mammalian subject. The subject may be a human, rat, dog or other mammal. Biopsy size ranged from 42 to 247 mg.

Skeletal muscle biopsy tissue is immediately placed in cold hypothermic medium (HypoThermosol (BioLife) supplemented with gentamicin sulfate (100 ng/ml, Roche)) and stored at 4° C. After 3 to 7 days, biopsy tissue is removed from storage and production is initiated. Any connective or non-muscle tissue is dissected from the biopsy sample. The remaining muscle tissue that is used for isolation is weighed. The tissue is minced in Hank's Balanced Salt Solution (HBSS), transferred to a conical tube, and centrifuged (2,500×g, 5 minutes). The pellet is resuspended in Digestion Enzyme solution (Liberase Blendzyme 4 (0.4-1.0 U/mL, Roche)). 2 mL of Digestion Enzyme solution is used per 100 mg of biopsy tissue and is incubated for 30 minutes at 37° C. on a rotating plate. The sample is then centrifuged (2,500×g, 5 minutes). The pellet is resuspended in culture medium and passed through a 70 μm cell strainer. The culture media used for the procedures described in this Example was Cambrex Endothelial Growth Medium EGM-2 basal medium supplemented with the following components: i. 10% (v/v) fetal bovine serum, and ii. Cambrex EGM-2 SingleQuot Kit, which contains: Insulin Growth Factor-1 (IGF-1), Basic Fibroblast Growth Factor (bFGF), Vascular Endothelial Growth Factor (VEGF), Epidermal Growth Factor (EGF), Hydrocortisone, Heparin, and Ascorbic Acid. The filtered cell solution is then transferred to a T25 culture flask and incubated for 30-120 minutes at 37° C. in 5% $CO_2$. Cells that attach to this flask are the "rapidly-adhering cells".

After incubation, the cell culture supernatant is removed from the T25 flask and placed into a 15 mL conical tube. The T25 culture flask is rinsed with 2 mL of warmed culture medium and transferred to the aforementioned 15 mL conical tube. The 15 mL conical tube is centrifuged (2,500×g, 5 minutes). The pellet is resuspended in culture medium and transferred to a new T25 culture flask. The flask is incubated for days at 37° C. in 5% $CO_2$ (cells that attach to this flask are the "slowly-adhering cells"). After incubation, the cell culture supernatant is aspirated and new culture medium is added to the flask. The flask is then returned to the incubator for expansion. Standard culture passaging is carried out from here on to maintain the cell confluency in the culture flask at less than 50%. Trypsin-EDTA (0.25%, Invitrogen) is used to detach the adherent cells from the flask during passage. Typical expansion of the "slowly-adhering cells" takes an average of 17 days (starting from the day production is initiated) to achieve an average total viable cell number of 37 million cells.

Once the desired cell number is achieved, the cells are harvested from the flask using Trypsin-EDTA and centrifuged (2,500×g, 5 minutes). The pellet is resuspended in BSS-P solution (HBSS supplemented with human serum albumin (2% v/v, Sera Care Life)) and counted. The cell solution is then centrifuged again (2,500×g, 5 minutes), resuspended with Cryopreservation Medium (CryoStor (Biolife) supplemented with human serum albumin (2% v/v, Sera Care Life Sciences)) to the desired cell concentration, and packaged in the appropriate vial for cryogenic storage. The cryovial is placed into a freezing container and placed in the −80° C. freezer. Cells are administered by thawing the frozen cell suspension at room temperature with an equal volume of physiologic saline and injected directly (without additional manipulation). The lineage characterization of the slowly adhering cell populations shows: Myogenic (87.4% CD56+, 89.2% desmin+), Endothelial (0.0% CD31+), Hematopoietic (0.3% CD45+), and Fibroblast (6.8% CD90+/CD56-).

Following disassociation of the skeletal muscle biopsy tissue, two fractions of cells were collected based on their rapid or slow adhesion to the culture flasks. The cells were then expanded in culture with growth medium and then frozen in cryopreservation medium ($3 \times 10^5$ cells in 15 μl) in a 1.5 ml eppendorf tube. For the control group, 15 μl of cryopreservation medium alone was placed into the tube. These tubes were stored at −80° C. until injection. Immediately prior to injection, a tube was removed from storage, thawed at room temperature, and resuspended with 15 μl of 0.9% sodium chloride solution. The resulting 30 μl solution was then drawn into a 0.5 cc insulin syringe with a 30 gauge needle. The investigator performing the surgery and injection was blinded to the contents of the tubes.

Cell count and viability was measured using a Guava flow cytometer and Viacount assay kit (Guava). CD56 was measured by flow cytometry (Guava) using PE-conjugated anti-CD56 antibody (1:50, BD Pharmingen) and PE-conjugated isotype control monoclonal antibody (1:50, BD Pharmingen). Desmin was measured by flow cytometry (Guava) on paraformaldehyde-fixed cells (BD Pharmingen) using a monoclonal desmin antibody (1:100, Dako) and an isotype control monoclonal antibody (1:200, BD Pharmingen). Fluorescent labeling was performed using a Cy3-conjugated anti-mouse IgG antibody (1:250, Sigma). In between steps, the cells were washed with permeabilization buffer (BD Pharmingen). For creatine kinase (CK) assay, $1 \times 10^5$ cells were plated per well into a 12 well plate in differentiation-inducing medium. Four to 6 days later, the cells were harvested by trypsinization and centrifuged into a pellet. The cell lysis supernatant was assayed for CK activity using the CK Liqui-UV kit (Stanbio).

Figure 1B:
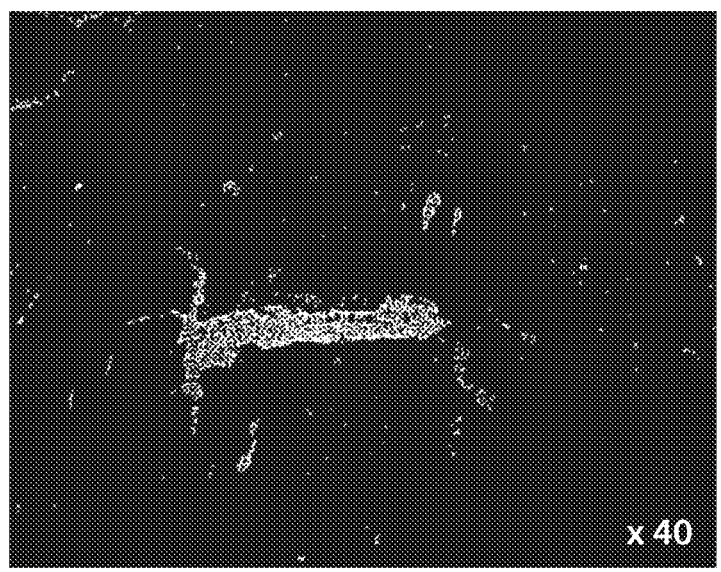

Example 3. Soft Tissue Augmentation of the Gastro-Esophageal Junction and Anal Sphincter Sprague-Dawley (SD) rats were prepared for surgery by anesthetizing with halothane using standard methods, and washing the surgical site with Betadine® solution. A midline abdomen incision was made to expose the gastroesophageal junction and anal sphincter. The soft tissue was injected with 10 μl of a suspension of muscle-derived progenitor cells, prepared pursuant to the methods of Example 1, in HBSS ($1$-$1.5 \times 10^6$ cells) using a Hamilton microsyringe. At day 3 post-injection, the area surrounding each injection site was excised, prepared for histochemical analysis, stained for β-galactosidase to determine the location and viability of the cells carrying the LacZ marker, examined microscopically, and photographed. Results of these experiments demonstrate that MDC compositions can be used as esophageal and anal sphincter bulking materials (FIGS. 1A and 1B) for the treatment of gastroesophageal reflux or fecal incontinence symptoms or conditions.

Example 4. MDC Implantation in the Lower Esophageal Sphincter for the Treatment of Gastro-Esophageal Reflux Disorder (GERD)

Most patients with GERD who are being considered for surgery have low lower esophageal sphincter (LES) pressure. We hypothesized that auto-transplantation of skeletal muscle-derived cells (MDC) into the LES may offer the ideal bulking therapy. To test this, we have performed experiments to test the potential of MDCs to survive and differentiate within the gastro intestinal smooth muscle in order to gain further knowledge on the biology of skeletal muscle transplantation in GI smooth muscle sphincters as well as to test the safety and feasibility of endoscopic injection of MDC in a large animal model.

Adult male Sprague-Dawley (SD) rats and adult male Beagle dogs were used. Rat-derived and dog-derived MDC were isolated using a single plate technique similar to the technique described in Example 2. MDCs were labeled with DiI, a lipophilic membrane stain that diffuses across the whole cell, (Invitrogen/Molecular Probes) before transplantation in order to be able to visualize the cells in the host tissue. Differentiation of grafted cells was assessed by immunofluorescence using specific antibodies to markers of the smooth muscle phenotype (smooth muscle actin) and of the skeletal muscle phenotype (skeletal muscle myosin).

Rat Experiments.

Figure 2A:
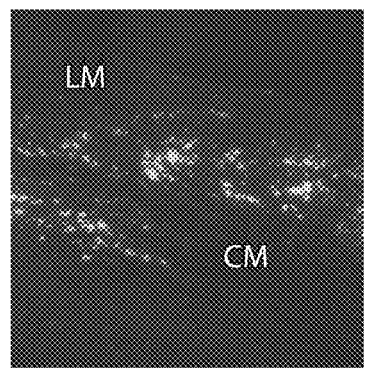
FIGS. 2A-2C show confocal fluorescent micrographs of rat pylorus one month after injection with DiI labeled rat MDCs.
Figure 2B:
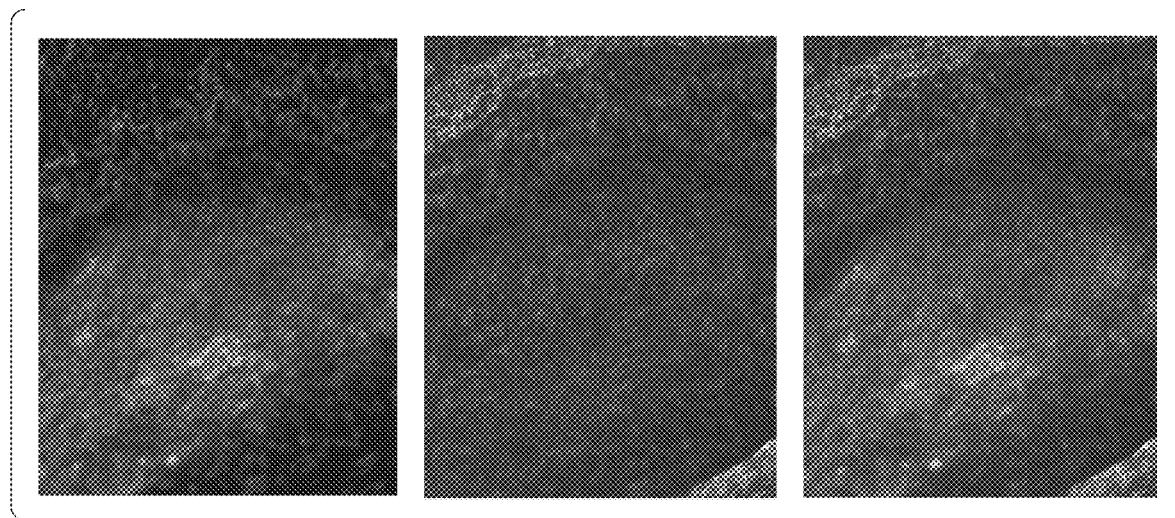

DiI-labeled rat-derived MDCs were injected bilaterally in the pyloric wall of rats using a 10 μl Hamilton syringe and survival and differentiation was assessed 1 month post-transplantation. Grafted cells were visualized based on DiI fluorescence and were found to be localized within the muscle wall and in the muscularis mucosa, as shown in FIG. 2A. Immunofluorescence analysis revealed weak expression of skeletal muscle myosin in grafted MDC and no expression of smooth muscle actin, as shown in FIGS. 2B (smooth muscle actin) and 2C (skeletal muscle myosin). MDC can survive and integrate into GI smooth muscle and they have potential for the treatment of a variety of conditions including GERD.

MDC Transplantation in a Canine Model of GERD.

In the first of a series of ongoing experiments, $4.0 \times 10^6$ of labeled canine MDC were injected into the LES of a Beagle dog using a standard variceal sclerotherapy needle delivered through an endoscope. The dog was treated with daily cyclosporine and two weeks later pH monitoring repeated and the esophagus examined histologically. A significant reduction of acid reflux was observed with the fraction of time with pH<4 decreasing from 26.5% to 1.5%. Transplanted MDC were seen (by immunofluorescence staining) adding bulk to the lower esophageal area, and were well integrated into the surrounding tissue particularly in the muscularis mucosa.

Figure 2C:
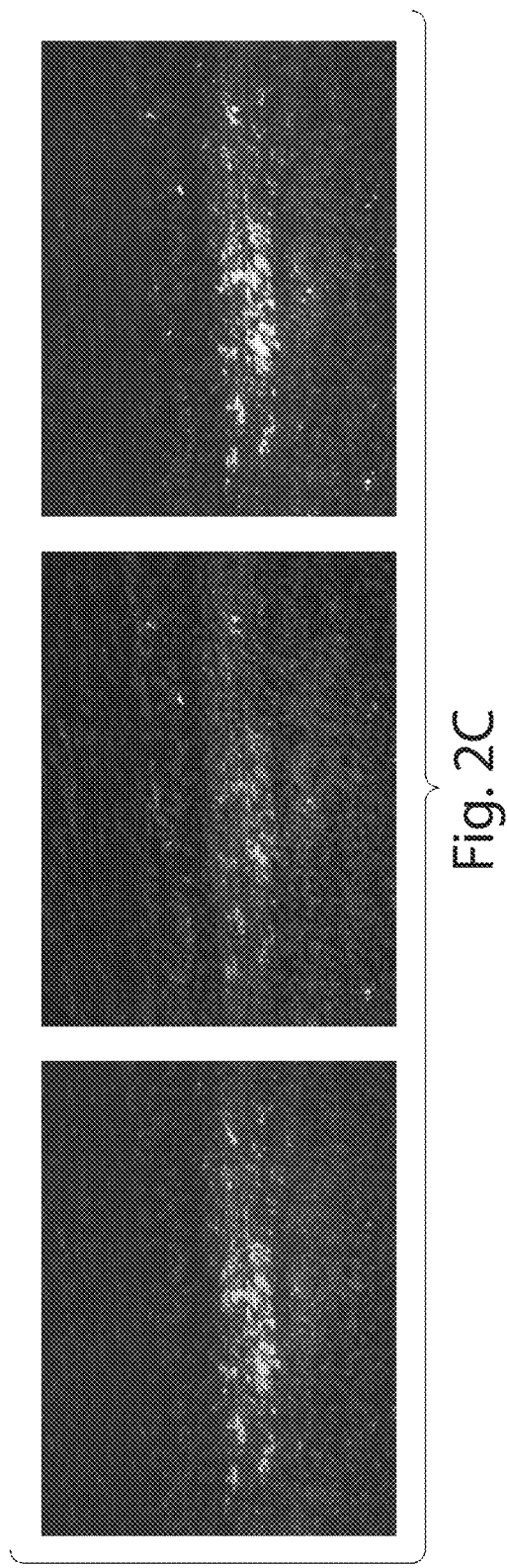

Example 5. MDC Implantation in the Lower Esophageal Sphincter Increase Contractility Organ bath analysis of the rat pyloric muscle revealed a significant increase in muscle contraction in response to acetylcholine after MDC transplantation as compared to saline-injected controls (FIG. 2).

Organ Bath Analysis of Pyloric Function.

Four weeks post-transplantation, rats were anesthetized and the pyloric region dissected out. Circular muscle strips were mounted between two L-shaped tissue hooks in 5 mL chambers containing Krebs buffer at 37° C. and continuously bubbled with 95% $O_2$, 5% $CO_2$. (Radnoti Glass Technology, Monrovia, Calif.). Tension was monitored with an isometric force transducer and recorded and analyzed by a digital recording system (Biopac Systems Inc., Santa Barbara, Calif.). Strips were stretched to 2 g (10 mN) and allowed to equilibrate for 30 minutes. Pyloric function was assessed by measuring the ability of the pyloric circular muscle to contract in response to acetylcholine. Acetylcholine (ACh) was added to the chambers from freshly prepared 100× stock solutions. The weight of the tissue was measured at the end of each session.

Comparisons between the groups was performed by measuring the area under the curve of the ACh-induced contraction (AUCC) for 1 minute and the baseline for 1 minute (AUCB), according to the following formula: (AUCC-AUCB)/weight of tissue (mg)=AUC/mg of tissue.

Rat-derived MDCs were labeled with CM-DiI (Invitrogen Co., Carlsbad, Calif.) according to Manufacturer's instruction to allow for the identification of grafted cells in the host tissue. Adult male Sprague-Dawley rats were deeply anesthetized using a combination of ketamine/xylazine, a midline incision was made and the pyloric region identified. DiI-labeled rat MDC were suspended in Dulbecco's PBS and injected bilaterally (50,000 cells/μl; 2 μl per site) in the pyloric wall using a 10 μl Hamilton syringe. Another set of rats received bilateral injections of Dulbecco's PBS and served as sham controls.

Figure 3:
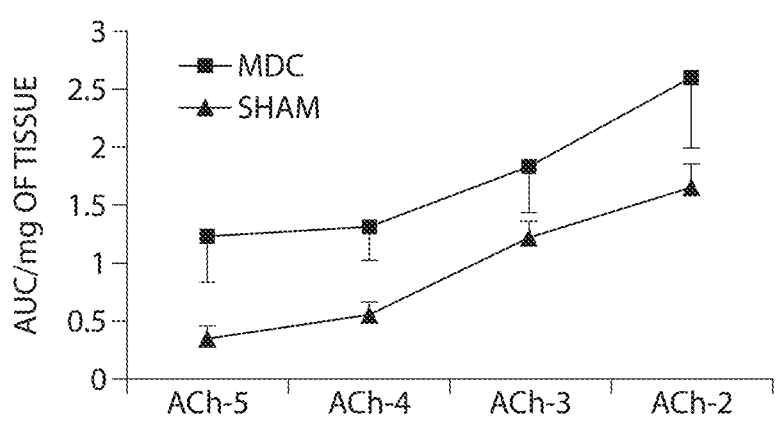
FIG. 3 is a graph showing dose-response effect of acetylcholine-induced contractions of rat pyloric circular muscle strips 4 weeks after MDC transplantation or vehicle injection (SHAM).

Organ bath analysis of the rat pyloric muscle revealed a significant increase in muscle contraction in response to acetylcholine after MDC transplantation as compared to saline-injected controls (FIG. 3). Analysis of the results by one-way ANOVA revealed a significant effect of MDC transplantation (P=0.002). Data are means+/−SEM. N=6 for MDC and 7 for SHAM.

Three Beagle dogs were evaluated for the effects of MDC injection on esophageal physiology. All underwent baseline esophageal manometry to measure LES pressure as well as pH monitoring using a Bravo system. Subsequently, $4.0 \times 10^6$ of DiI-labeled canine MDC were suspended in 5 ml of sterile physiological saline and injected into the LES of all three Beagle dogs using a variceal sclerotherapy needle. The dogs were treated with cyclosporine daily 100 mg/day and manometry was performed 1-2 weeks later on all three dogs.

Figure 4A:
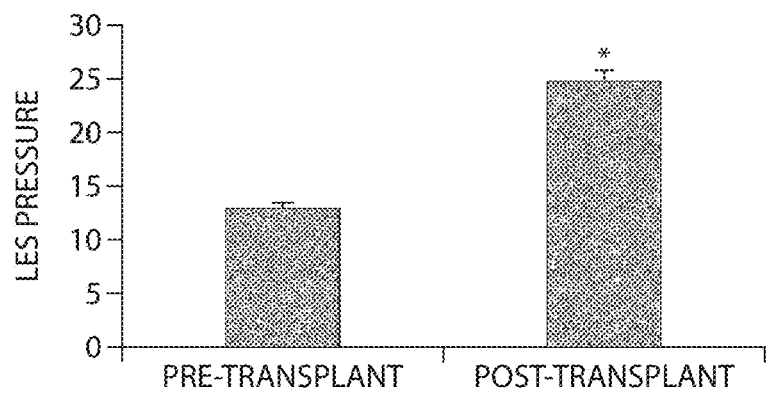
FIG. 4A is a bar graph that shows lower esophageal sphincter (LES) pressure measured in Beagle dogs before and 4 weeks after transplantation of dog MDCs.
Figure 4B:
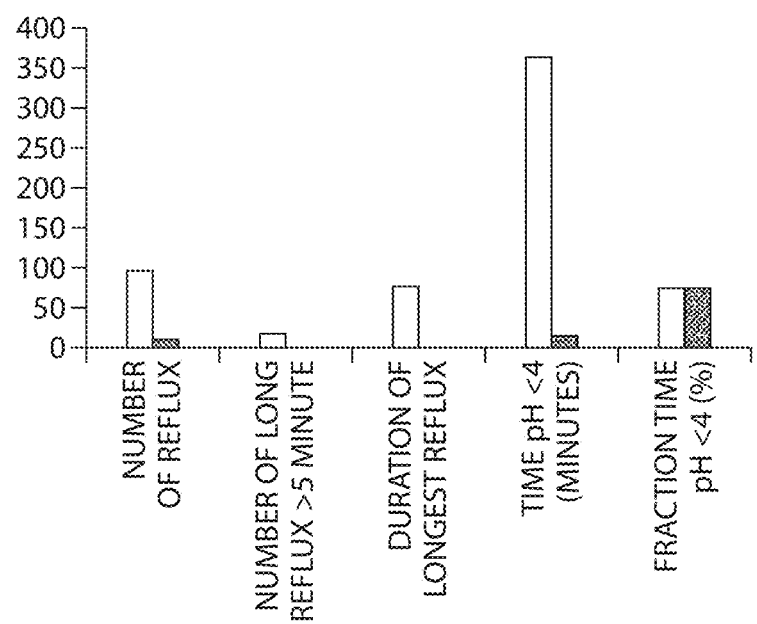
FIG. 4B is a bar graph showing dog LES pH monitoring in one Beagle dog measured before (clear column) and 2 weeks after MDC transplantation (filled columns).
Figure 5A:
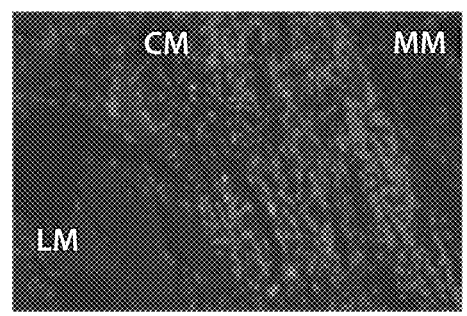
FIG. 5A-C show confocal fluorescent micrographs of representative images of grafted dog MDC in cross sections of dog LES 4 weeks after transplantation. DiI-labeled MDC are shown in red. Immunofluorescence analysis for the expression of skeletal muscle myosin (B) and smooth muscle actin (C). Magnification=20× (A) and 40× (B and C). LM: Longitudinal Muscle; CM: Circular Muscle; MM: Muscularis Mucosa.
Figure 5B:
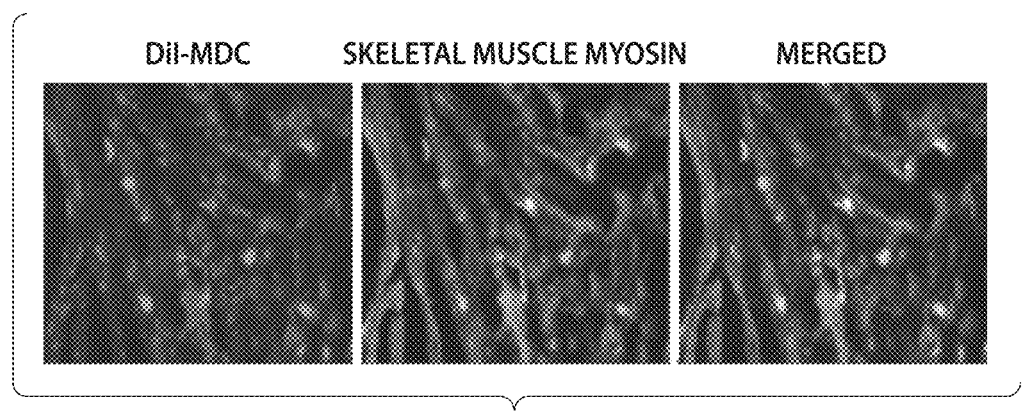
Figure 5C:
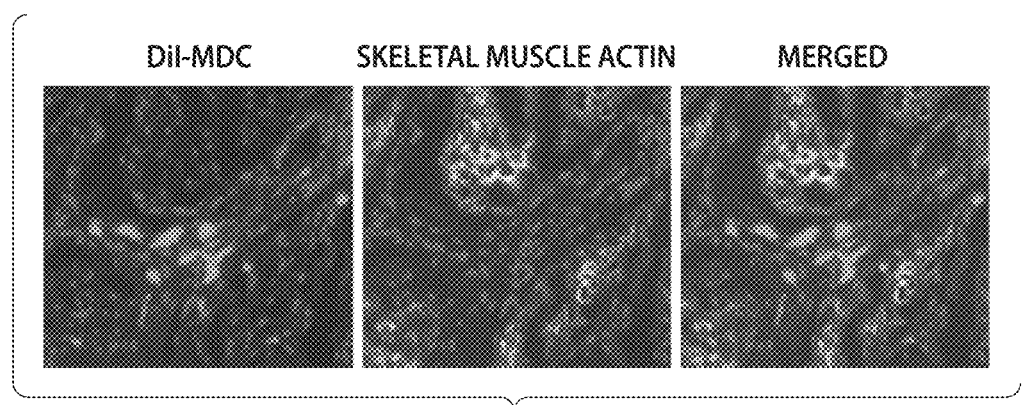

In dogs, MDC injection resulted in a significant increase in baseline LES pressure (FIG. 4A). Data are means+/−SEM; N=3. P<0.01 by Student's T-test. Further in one dog with significant baseline acid reflux, MDC injection resulted in a dramatic reduction of acid reflux, with the fraction of time with pH<4 decreasing from 26.5% to 1.5%; the number of refluxes measured was reduced from 95 in 22 hours 48 minutes to 11 in 18 hours 28 minutes; the number of refluxes lasting longer than 5 minutes was reduced from 16 in 22 hours 48 minutes to 0 in 18 hours 28 minutes; and the duration of longest reflux was reduced from 76 minutes to 2 minutes. (FIG. 4B). Transplanted MDC were seen adding bulk to the lower esophageal area, and were well integrated into the surrounding tissue particularly in the muscularis mucosa. Grafted cells showed positive immunoreactivity for skeletal muscle myosin and not for smooth muscle actin (FIG. 5).

All patent applications, patents, texts, and literature references cited in this specification are hereby incorporated herein by reference in their entirety to more fully describe the state of the art to which the present invention pertains.

As various changes can be made in the above methods and compositions without departing from the scope and spirit of the invention as described, it is intended that all subject matter contained in the above description, shown in the accompanying drawings, or defined in the appended claims be interpreted as illustrative, and not in a limiting sense.

What is claimed is:

1. A method of increasing lower esophageal sphincter pressure in a mammalian subject at risk of developing gastro-esophageal reflex disease, the method comprising:
   (a) isolating skeletal muscle cells from the mammalian subject;
   (b) cooling the cells to a temperature lower than 10° C. and storing the cells for 1-7 days;
   (c) suspending the mammalian skeletal muscle cells in media in a first cell culture container for between 30 and 120 minutes;
   (d) decanting the media from the first cell culture container to a second cell culture container;
   (e) allowing the remaining cells in the media to attach to the walls of the second cell culture container;
   (f) isolating the cells from the walls of the second cell culture container, wherein the isolated cells are muscle-derived progenitor cells (MDCs);
   (g) culturing the isolated MDCs to expand their number;
   (h) freezing the MDCs to a temperature below −30° C.;
   (i) thawing the MDCs; and
   (j) administering the MDCs to the esophagus of the mammalian subject;
   thereby increasing lower esophageal sphincter pressure by at least about 50% in the mammalian subject.

2. The method of claim 1, wherein the skeletal muscle cells are isolated from the mammalian subject before a gastro-esophageal reflux disease begins in the mammalian subject.

3. The method of claim 1, wherein the increase in lower esophageal sphincter pressure is increased by at least about 100%.

4. The method of claim 1, wherein the MDCs are administered by injecting them into the esophagus.

5. The method of claim 1, wherein the administering step involves injecting the MDCs into the lower esophageal sphincter.

6. The method of claim 1, wherein the mammal is a human.

7. A method of increasing lower esophageal sphincter pressure in a mammalian subject comprising:
   (a) isolating skeletal muscle cells from the mammalian subject,
   (b) suspending the mammalian skeletal muscle cells in media in a first cell culture container for between 30 and 120 minutes;
   (c) decanting the media from the first cell culture container to a second cell culture container;
   (d) allowing the remaining cells in the media to attach to the walls of the second cell culture container;
   (e) isolating the cells from the walls of the second cell culture container, wherein the isolated cells are muscle-derived progenitor cells (MDCs); and
   (f) administering the MDCs to the esophagus of the mammalian subject;
   thereby increasing lower esophageal sphincter pressure in the mammalian subject.

8. The method of claim 7, wherein the increase in lower esophageal sphincter pressure is increased by at least about 100%.

9. The method of claim 7, wherein the MDCs are administered by injecting them into the esophagus.

10. The method of claim 9, wherein the MDCs are injected into the lower esophageal sphincter.

11. The method of claim 7, wherein the mammal is a human.

12. The method of claim 7, wherein the MDCs are cultured to expand their number before being administered to the esophagus of the mammalian subject.

* * * * *